(12) United States Patent
Ogasawara

(10) Patent No.: US 11,018,691 B2
(45) Date of Patent: *May 25, 2021

(54) INCREASING STORAGE CAPACITY AND DATA TRANSFER SPEED IN GENOME DATA BACKUP

(71) Applicant: INTERNATIONAL BUSINESS MACHINES CORPORATION, Armonk, NY (US)

(72) Inventor: Takeshi Ogasawara, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 6 days.

This patent is subject to a terminal disclaimer.

(21) Appl. No.: 16/514,273

(22) Filed: Jul. 17, 2019

(65) Prior Publication Data
US 2019/0341929 A1 Nov. 7, 2019

Related U.S. Application Data

(63) Continuation of application No. 14/743,604, filed on Jun. 18, 2015, now Pat. No. 10,419,020.

(51) Int. Cl.
G06F 16/00 (2019.01)
H03M 7/30 (2006.01)
(Continued)

(52) U.S. Cl.
CPC ......... H03M 7/3059 (2013.01); G06F 16/113 (2019.01); G06F 16/1727 (2019.01);
(Continued)

(58) Field of Classification Search
CPC ......... G06F 17/30073; G06F 17/30138; G06F 17/30153; G06F 16/1727; G06F 16/1744; G06F 16/113; H03M 7/3059
(Continued)

(56) References Cited

U.S. PATENT DOCUMENTS

| 7,260,642 B2 * | 8/2007 | Chang | H04L 29/06027 |
| | | | 375/E7.176 |
| 2010/0074543 A1 * | 3/2010 | Torai | H04N 19/593 |
| | | | 382/239 |
| 2014/0214780 A1 * | 7/2014 | Lange | G06F 16/1744 |
| | | | 707/693 |

FOREIGN PATENT DOCUMENTS

| JP | 05-225308 A | 9/1993 |
| JP | 07-322076 A | 12/1995 |

(Continued)

OTHER PUBLICATIONS

List of IBM Patents or Patent Applications Treated as Related dated Jul. 17, 2019, 2 pages.

*Primary Examiner* — Monica M Pyo
(74) *Attorney, Agent, or Firm* — Tutunjian & Bitetto, P.C.; Randall Bluestone

(57) ABSTRACT

Methods and systems for storing data include compressing data inflated from a first compression format into a second format using a processor and verifying contents of the data concurrently with compressing the data. Compression is aborted responsive to a failure of the content verification, but an output of the compression is stored to a tape drive until the compression is aborted. The tape drive is rolled back to a file start position after the compression is aborted and compression of any remaining uncompressed data is skipped after the compression is aborted. The data is stored to the tape drive after rolling the tape drive back.

20 Claims, 2 Drawing Sheets

(51) Int. Cl.
*G06F 16/17* (2019.01)
*G06F 16/174* (2019.01)
*G06F 16/11* (2019.01)
*G16B 50/00* (2019.01)

(52) U.S. Cl.
CPC ......... *G06F 16/1744* (2019.01); *G16B 50/00* (2019.02); *H03M 7/30* (2013.01); *H03M 7/607* (2013.01); *H03M 7/6041* (2013.01)

(58) Field of Classification Search
USPC ....................................................... 707/693
See application file for complete search history.

(56) References Cited

FOREIGN PATENT DOCUMENTS

| | | | |
|---|---|---|---|
| JP | 08-116274 | A | 5/1996 |
| JP | 10-215228 | A | 8/1998 |
| JP | 2002-164796 | A | 6/2002 |
| JP | 2003-188735 | A | 7/2003 |
| JP | 2012-094141 | A | 5/2012 |
| JP | 2013-239162 | A | 11/2013 |
| WO | 2007-026484 | A1 | 3/2007 |

* cited by examiner

INCREASING STORAGE CAPACITY AND DATA TRANSFER SPEED IN GENOME DATA BACKUP

BACKGROUND

Technical Field

The present invention relates to genetic sequencing and, more particularly, to storage techniques for large volumes of genome data.

Description of the Related Art

Historically, genetic sequencing was a slow process that generated genome data at a rate that could be easily accommodated by existing storage technologies. Next generation sequencing technologies, however, produce genome data much more rapidly, and the rate of data production is increasing at a rate that outstrips storage capacity technology advances. For example, the European Bioinformatics Institute estimates that their storage capacity needs double year-to-year. The capacity of storage technologies, meanwhile, increases roughly in accordance with Moore's law, doubling every eighteen months.

In the early stages of generating genomic data, data is often produced in a human-readable (e.g., ASCII) format called SAM. However, SAM is very inefficient and produces files that are terabytes in size. These SAM files are often converted to BAM, which is a binary form and is typically compressed. A compressed BAM file is a sequence of compressed BAM blocks, with uncompressed BAM blocks each having about 64 kb of data. However, in the face of the tremendous rate at which genomic data is generated, even BAM files are growing unsuitable for storage.

Superior data management techniques are therefore needed. If disks are not large enough to store all of the available data, an additional cost is incurred by file management in determining which files should be deleted and which should be preserved.

Tape storage is frequently used for archiving genome data. Standard tape devices often implement hardware data compression and can perform real-time compression of archived data. However, data compression by tape devices is not effective for genome data that has already been compressed using, e.g., BAM compression.

SUMMARY

A method for storing data includes compressing data inflated from a first compression format into a second format using a processor and verifying contents of the data concurrently with compressing the data. Compression is aborted responsive to a failure of the content verification, but an output of the compression is stored to a tape drive until the compression is aborted. The tape drive is rolled back to a file start position after the compression is aborted and compression of any remaining uncompressed data is skipped after the compression is aborted. The data is stored to the tape drive after rolling the tape drive back.

A system for storing data includes a compression module having a processor configured to create blocks from data inflated from a first compression format for a second compression format that is different from the first compression format and to compress the blocks in the second format. The system also includes a verification module configured to verify contents of the blocks concurrently with compression of the blocks, wherein the compression module is further configured to abort compression responsive to a failure of content verification. The tape drive of the system is configured to store an output of the compression until compression is aborted, to roll back to a file start position after the compression is aborted, skip compression of any remaining uncompressed blocks after the compression is aborted, and to store the received data after rolling back.

A non-transitory computer readable storage medium includes a computer readable program for storing data, that when executed on a computer causes the computer to perform the steps of: compressing data inflated from a first compression format into a second compression format that is different from the first compression format using a processor, verifying contents of the data concurrently with compressing the data, and aborting compression responsive to a failure of the content verification. When executed on a computer, the computer readable program of the computer readable storage medium also causes the computer to perform the steps of: storing an output of the compression to a tape drive until the compression is aborted, rolling the tape drive back to a file start position after the compression is aborted, skipping compression of any remaining uncompressed blocks after the compression is aborted and storing the received data to the tape drive after rolling the tape drive back.

These and other features and advantages will become apparent from the following detailed description of illustrative embodiments thereof, which is to be read in connection with the accompanying drawings.

BRIEF DESCRIPTION OF THE SEVERAL VIEWS OF THE DRAWINGS

The disclosure will provide details in the following description of preferred embodiments with reference to the following figures wherein.

DETAILED DESCRIPTION

Embodiments of the present invention take files that are already compressed under, e.g., BAM compression, and transparently convert them to a more efficient compression format before archival. In one particular embodiment, the files are converted to the CRAM compression format, which produces significantly better compression ratios for genome data than BAM compression. Pipeline stages are created for type identification, compression, and verification related to the target compression format that exploit parallelism in the file structure to accelerate the processes, ensuring file validity.

Figure 1:
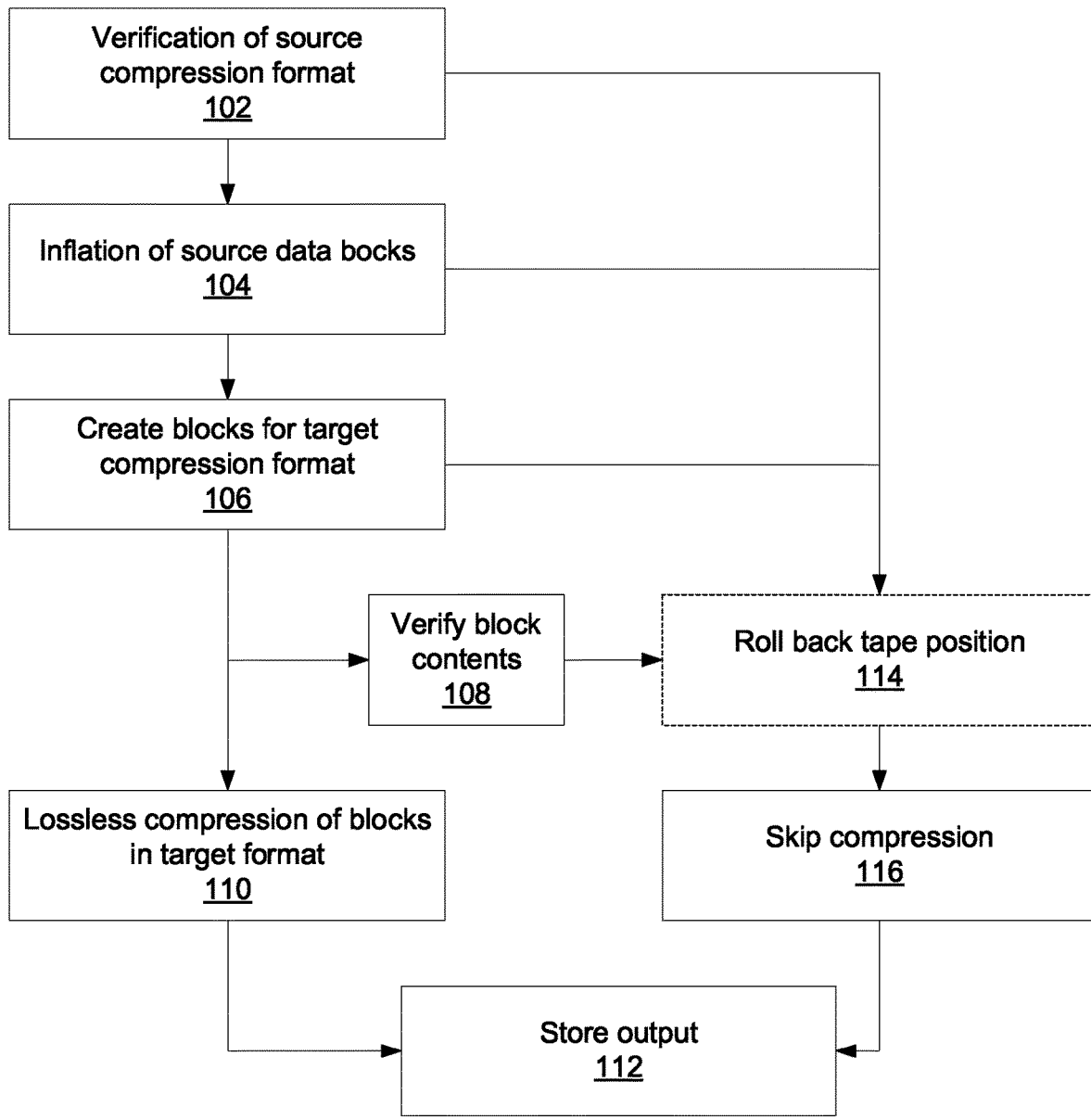
FIG. 1 is a block/flow diagram of a method for data storage in accordance with the present principles.

Referring now to the drawings in which like numerals represent the same or similar elements and initially to FIG. 1, a method for genome data storage is shown. While the present embodiments are discussed specifically in the context of genome data, it should be understood that any appropriate data type may be used. Block 102 receives data for storage that is compressed using a source compression format such as, e.g., BAM compression, and verifies the format of the received data. In particular, block 102 identifies block headers at non-fixed positions on the archived file and checks if the headers conform to the source compression format specification. If the source compression format is correctly identified, block 104 inflates the compressed blocks of the source format into uncompressed data.

Block 106 takes the inflated data and uses it to create blocks in the target compression format. In one particular embodiment, CRAM compression is used as the target compression format. This may be performed by collecting data blocks of a same type into a CRAM block. Block 108 verifies the blocks' contents in the background by, e.g., checking whether the contents of the CRAM blocks are the same as the contents of the inflated data.

Concurrently with the verification of block 108, block 110 performs lossless compression of the blocks in, e.g., CRAM format, with a specific compression algorithm being selected depending on the type of each block. Block 112 then transfers the compressed blocks to a storage device. The storage device may be, e.g., a tape storage device. Block 112 completes archiving the input file and records a file archive completion as CRAM.

At several points in this process, a step may fail. For example, the input file might not have the expected source compression format headers in block 102, the inflation of data in block 104 may fail, or the creation of blocks in the target compression format may fail either during creation in block 106 or during verification in block 108. In each of these cases, assuming a tape drive is used for storage, processing goes to block 114. At block 114, the tape position is rolled back to a point before the file backup began. Block 116 then skips any remaining compression steps and block 112 stores, instead of a recompressed file, the original input file. Thus if recompression fails at any point, the information is stored in its source format.

Notably, verification of the blocks created in 106 is performed alongside compression of the blocks in 110. The data format is converted for compression speculatively, without foreknowledge of the underlying data, by performing the data integrity check of block 108 in the background. There is the possibility that only the end user knows the format of the data in the system and there is further the possibility that the data does not always comply with the format specifications. With conventional approaches, data integrity is checked first to determine whether a given data block is in the desired format, before processing the data. However, pre-verification takes a significant amount of time before the conversion may be performed and might not be completed within a target period. Instead, the present embodiments perform data format conversion in block 110 right away, without waiting for verification in block 108 to complete. If the data verification in block 108 finds that the current data cannot be compressed, then the ongoing compression of block 110 is canceled.

Although BAM and CRAM compression formats are discussed herein for the purpose of illustration, it should be recognized that any appropriate compression format(s) may be used in their stead. BAM is a very common format for storing genome data, while CRAM produces file sizes that are generally smaller than those produced by the popular BAM compression format.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 2:
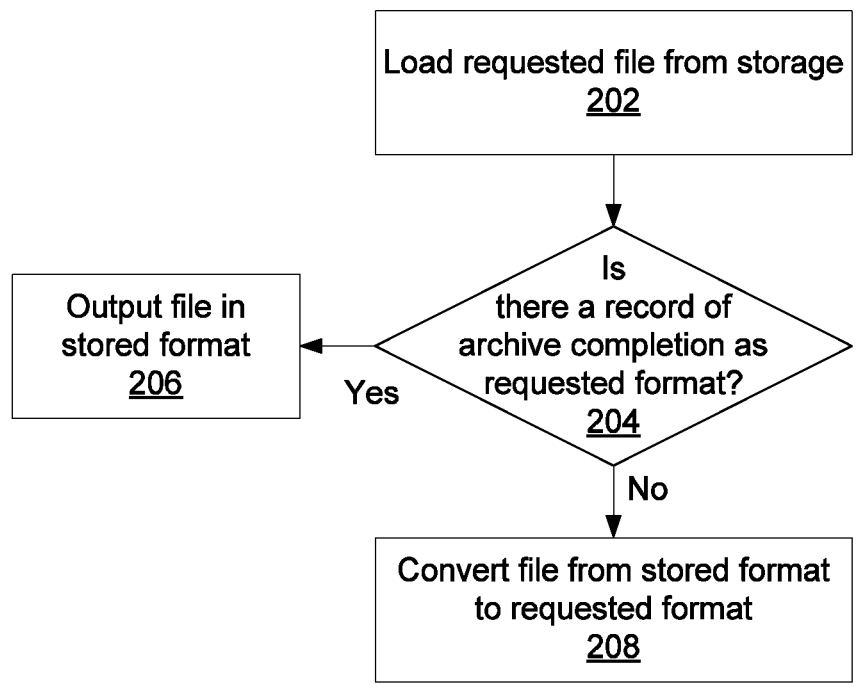
FIG. 2 is a block/flow diagram of a method for data retrieval in accordance with the present principles.

Referring now to FIG. 2, a method for recalling stored data is shown. Block 202 loads the requested file from the storage device, which may for example be a tape drive. Block 204 determines whether the loaded file is in a requested format by, e.g., checking a file archive for a record of completion for the format. If the file is in the requested format (e.g., if the file was stored in a CRAM format and such a format was requested), then block 206 outputs the stored file as-is. If a different format is requested, for example if the file was stored in a CRAM format and a BAM format is requested, then block 208 converts the stored format to the requested format. The speed of restoring archived files is increased by the storage of data in more efficient compression formats, as the transfer speed of retrieving the file from storage is the bottleneck. Thus, smaller files being stored results in much more efficient loading.

Figure 3:
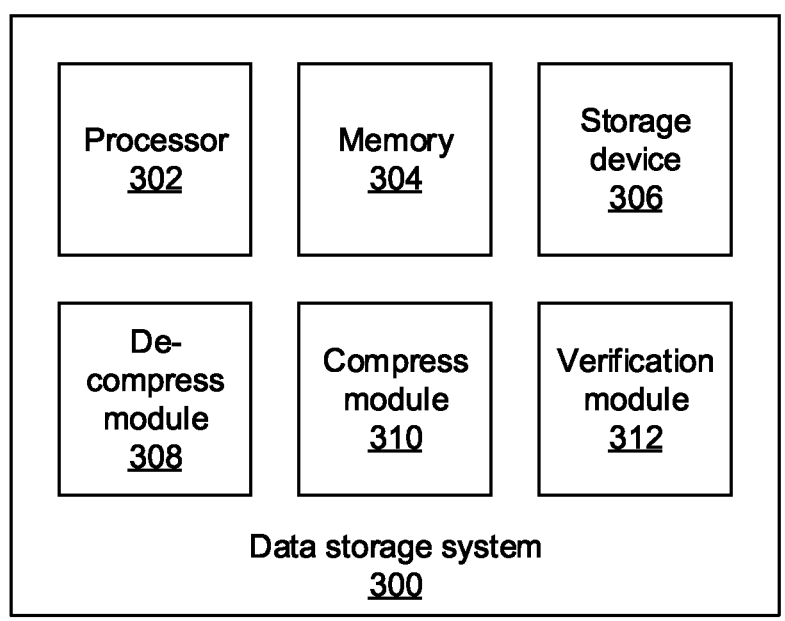
FIG. 3 is a block diagram of a system for data storage in accordance with the present principles.

Referring now to FIG. 3, a system 300 for data storage is shown. A hardware processor 302 performs computations related to compression, decompression, and storage of data while a memory 304 stores information during processing. A storage device 306, distinct from the memory 304, provides archival for data that has been processed. It is specifically contemplated that the storage device 306 may be a tape-based storage device, but it should be understood that any appropriate storage device may be used instead. In the case of a tape-based storage device, the storage device 306 may have built-in compression abilities and may have the ability to roll-back to a previous point on the tape in case of compression failure.

A decompress module 308 accepts input data in a first compression format and decompresses/inflates the data using the processor 302. A compress module 310 then re-compresses the data in a second compression format using the processor 302. A verification module 312 performs verification of the data format concurrently with the operation of the compression module 310 to ensure that the data being processed is of the expected format. If the operation of any of the decompress module 308, the compress module 310, or the verification module 312 fails, the storage device 306 rolls back to a starting position and records the original data. Otherwise, the storage device 306 stores the re-compressed data in the second compression format.

Having described preferred embodiments of a system and method for increasing storage capacity and data transfer speed in genome data backup (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

The invention claimed is:

1. A method for storing data, comprising:
   compressing data inflated from a first compression format into a second format using a processor;
   verifying contents of the data concurrently with compressing the data;
   aborting compression responsive to a failure of the content verification;
   storing an output of the compression to a tape drive until the compression is aborted;
   rolling the tape drive back to a file start position after the compression is aborted;
   skipping compression of any remaining uncompressed data after the compression is aborted; and
   storing the data to the tape drive after rolling the tape drive back.

2. The method of claim 1, wherein storing the data to the tape drive after rolling the tape drive back comprises storing the data in the first compression format.

3. The method of claim 2, wherein the first compression format is BAM and the second compression format is CRAM.

4. The method of claim 1, further comprising collecting data blocks of a same type into blocks suitable for use with the second compression format prior to compressing the data into the second compression format.

5. The method of claim 1, wherein compressing the data in the second format comprises performing a lossless compression.

6. The method of claim 1, wherein verifying contents of the data comprises determining whether contents of the compressed data in the second compression format is the same as contents of the inflated data.

7. The method of claim 1, wherein the file size of the second compression format is smaller than the file size of the first compression format.

8. A system for storing data, comprising:
   a compression module comprising a processor configured to create blocks from data inflated from a first compression format for a second compression format that is different from the first compression format and to compress the blocks in the second format;
   a verification module configured to verify contents of the blocks concurrently with compression of the blocks, wherein the compression module is further configured to abort compression responsive to a failure of content verification; and
   a tape drive configured to store an output of the compression until compression is aborted, to roll back to a file start position after the compression is aborted, skip compression of any remaining uncompressed blocks after the compression is aborted, and to store the received data after rolling back.

9. The system of claim 8, wherein the verification module is further configured to verify original data as being valid data in the first compression format.

10. The system of claim 9, wherein the verification module is further configured to identify block headers at non-fixed positions in the received data to verify the original data.

11. The system of claim 8, wherein the compression module is further configured to collect data blocks of a same type into blocks suitable for use with the second compression format.

12. The system of claim 8, wherein the compression module is further configured to perform a lossless compression.

13. The system of claim 8, wherein the verification module is further configured to determine whether contents of the compressed data in the second compression format is the same as contents of the inflated data.

14. The system of claim 8, wherein the first compression format is BAM.

15. The system of claim 8, wherein the second compression format is CRAM.

16. A non-transitory computer readable storage medium comprising a computer readable program for storing data, wherein the computer readable program when executed on a computer causes the computer to perform the steps of:
   compressing data inflated from a first compression format into a second compression format that is different from the first compression format using a processor;
   verifying contents of the data concurrently with compressing the data;
   aborting compression responsive to a failure f the content verification;
   storing an output of the compression to a tape drive until the compression is aborted;
   rolling the tape drive back to a file start position after the compression is aborted;
   skipping compression of any remaining uncompressed blocks after the compression is aborted; and
   storing the received data to the tape drive after rolling the tape drive back.

17. The non-transitory computer readable storage medium of claim 16, wherein storing the data to the tape drive after rolling the tape drive back comprises storing the data in the first compression format.

18. The lion-transitory computer readable storage medium of claim 16, wherein the file size of the second compression format s smaller than the file size of the first compression format.

19. The non-transitory computer readable storage medium of claim 16, wherein the first compression format is BAM.

20. The non-transitory computer readable storage medium of claim 16, wherein the second compression format is CRAM.

* * * * *